United States Patent [19]

Seiler et al.

[11] 4,060,539
[45] Nov. 29, 1977

[54] SULFUROUS ORGANIC SILICON COMPOUNDS, A PROCESS FOR THEIR PREPARATION, AND THEIR USE AS ADHESIVIZING AGENTS

[75] Inventors: Claus-Dietrich Seiler, Rheinfelden; Hans-Joachim Vahlensieck, Wehr; Jürgen Amort, Troisdorf-Sieglar, all of Germany

[73] Assignee: Dynamit Nobel Aktiengesellschaft, Troisdorf, Germany

[21] Appl. No.: 660,952

[22] Filed: Feb. 24, 1976

[30] Foreign Application Priority Data

Mar. 1, 1975 Germany .............................. 2508931

[51] Int. Cl.² ................................................ C07F 7/18
[52] U.S. Cl. ............................................. 260/448.8 R
[58] Field of Search ................................. 260/448.8 R

[56] References Cited

U.S. PATENT DOCUMENTS 3,621,046  11/1971  Berger et al. ................. 260/448.8 R
3,632,826  1/1972   Berger ......................... 260/448.8 R X

*Primary Examiner*—Paul F. Shaver
*Attorney, Agent, or Firm*—Burgess, Dinklage & Sprung

[57] ABSTRACT

A sulfurous organosilicon compound of the general formula

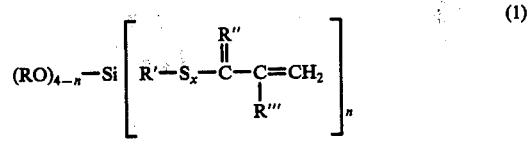

in which
  R represents a $C_{1-4}$ alkyl, a cycloalkyl, a $C_{1-4}$ alkyloxyalkyl or a phenyl radical,
  R' = a branched or unbranched alkylene radical of 1-6 carbon atoms, or a phenylene or benzylene radical,
  R" = oxygen or sulfur atom,
  R'" = hydrogen or $CH_3$,
  X = 1 or 2, and
  n = 1 or 2, processes for its production and its use as an adhesivizing agent to join inorganic substances to organic substances.

18 Claims, No Drawings

SULFUROUS ORGANIC SILICON COMPOUNDS, A PROCESS FOR THEIR PREPARATION, AND THEIR USE AS ADHESIVIZING AGENTS

FIELD OF THE INVENTION

The subject matter of the present invention is sulfurous organic silicon compounds which are suitable as adhesivizing agents between organic and inorganic materials. The invention further concerns methods of preparing the sulfurous organic silicon compounds and their use as adhesivizing agents.

SUMMARY OF THE INVENTION

The new sulfurous organosilicon compounds are characterized by the following general formula

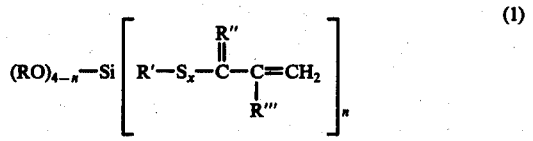

(1)

in which
R represents a $C_{1-4}$ alkyl, a cycloalkyl, e.g., C 6 to C 8 cycloalkyl, a $C_{2-4}$ alkyloxyalkyl or a or a phenyl radical,
R′ = a branched or unbranched alkylene radical of 1−6 carbon atoms, or a substituted or unsubstituted phenylene or benzylene radical,
R″ = oxygen or sulfur atom,
R‴ = hydrogen or $CH_3$,
x = 1 or 2, and
n = 1 or 2.

The invention further relates to the siloxanes developed by hydrolysis of the compound of formula 1 which siloxanes have the formula

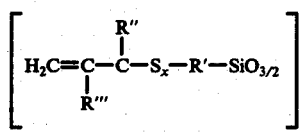

By the method of the invention, the sulfurous organosilicon compounds of the above formula are obtained by producing a reaction in the cold, e.g., −20° to +10° C, in the presence of polymerization inhibitors and tertiary amines, between the corresponding mercaptoalkyl-silicon compounds of the general formula

(2)

wherein R and R′ have the same meaning as in formula 1 and a methacrylic acid or its derivatives such as a saturated or unsaturated ester or acid halide, acrylic acid or its derivatives such as a saturated or unsaturated ester or acid halide, a monothiomethacrylic or monothioacrylic acid, saturated or unsaturated acid, or acid halide or a compound of the general formula

(3)

wherein R″ and R‴ have the meaning given in formula 1 and X represents a reactive group such as Cl, Br, —$NH_2$ or $CH_3O$ hydrazide amido. The reactive group X should be in a position to react with the proton on the sulfur atom. The H—X bond thus becomes free and an S—C bond is formed.

Examples of particularly suitable mercaptosilicon compounds are β-mercaptoethyltrimethoxysilane or γ-mercaptopropyltrimethoxysilane. However, the corresponding ω-mercaptobutyl or -hexyl or p-mercaptophenyltrimethoxy or triethoxysilanes can also be used. These compounds are prepared by generally known methods.

Also contemplated are the siloxanes produced by hydrolysis of the new sulfurous organosilicon compounds of formula 1 above. The hydrolysis of these organosilicon compounds there is formed through a condensation reaction the siloxanes of the above formula. Generally speaking, a partial or complete hydrolysis can be effected depending upon the desired degree of condensation. Where a partial hydrolysis is to be effected less than a full stoichiometric amount of water is present. Where full condensation to a fully condensed siloxane is desired water is present in at least a stoichiometric amount.

Generally speaking the hydrolysis can be conducted at temperatures between 0° and 100° C although room temperature is suitable. It is conducted at a pH of between 3 and 8. While subatmospheric and superatmospheric pressures can be employed during the condensation it is suitable to carry out the condensation at room temperature. Other process paramaters for the production of the corresponding siloxanes include the following:

The alcohol; splitt off during the hydrolysis, is distilled during or at the end of the hydrolysis.

Typical acrylate and methacrylate compounds that are used are methacrylic acid chloride, acrylic acid chloride.

However, the $C_{1-4}$ alkyl esters of acrylic or methacrylic acid can also be used as compounds of General Formula 3. The preferred esters are the methyl esters.

The temperatures necessary in the reaction, and the choice of the solvent and of any catalysts that may be necessary, are to be adapted to the special nature of the acrylic and methacrylic compounds involved. It is thus recommendable, when using the acid halides of methacrylic or acrylic acid, to perform the reactions in the presence of tertiary amines and polymerization inhibitors, and at temperatures around 0° C, e.g., −20° to +10° C. Generally, the tertiary amine is present in stoichiometric amounts, based on the acrylic compound. When esters of methacrylic and acrylic acid are used, however, it is advantageous to work in the presence of known transesterification catalysts and polymerization inhibitors and at temperatures between 40° and 60° C, under a vacuum if necessary.

Typical transesterification catalysts are, for example, titanic esters; typical polymerization inhibitors that can be used for the process of the invention are hydroquinone and di-tert.-butyl paracresol. These catalysts are employed in an amount of 0.1 to 5.0 weight percent, based on the weight of the reaction mixture.

The new sulfurous organic silicon compounds can also be prepared by producing a reaction, in the presence of the the above-named inhibitors and platinum compounds, and in the presence or absence of inert organic solvents, between alkenylthioacrylate and alkenylthiomethacrylate compounds of the general formula

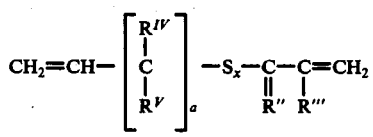

wherein
R" = an oxygen or sulfur atom
R'" = a hydrogen atom or methyl radical
R$^{IV}$ and R$^V$ = same or different = H, alkyl, e.g., C$_1$–C$_3$ alkyl, group, or phenyl group and
a = 1 and 2
and alkoxyhydrogen silanes of the general formula $$(RO)_{4-b}-SiH_b$$

wherein
b = 1 or 2,
R = C$_1$ to C$_4$ alkyl
Typical representatives of the alkenylthioacrylates and alkenylthiomethacrylates are the following:

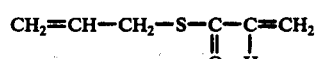 (6)

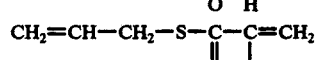 (7)

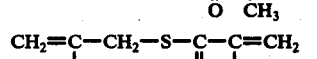 (8)

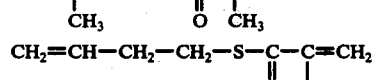 (9)

Especially suitable alkoxysilanes are trimethoxysilane, triethoxysilane, dimethoxysilane and diethoxysilane. The reaction, however, will also take place if tributoxysilane or triethoxymethoxysilane is used.

The platinum compounds are H$_2$Pt Cl$_6$ or complex Pt(IV) compounds, such as for example the platinum mesityl oxide complex compound as described in German Federal Pat. No. 1,937,904 hereby incorporated herein by reference.

The polymerization inhibitors can be compounds such as hydroquinone, quinone in conjunction with hydroquinone and aminophenols. The inhibitors are present in the reaction mixture in amount 1 to 10 weight percent.

The silanes of the invention are soluble in low concentration in an aqueous medium with hydrolysis, and they can be applied to solid inorganic surfaces of fillers and reinforcing substances, oxides and metals, by dipping, brushing or spraying, and can be solidified by a drying procedure. However, solvents containing water, in which the silane is dissolved, can also be used for the pretreatment. Other solvents for the silane include: Alcohols, such as Methanol, Ethanol and higher alcohols with 3 to 10 C-atomes, Ketones, such as Methylethylketone and others.

Such a solution of silane can be used for application of the silane to a surface of an inorganic material.

For the preparation of reinforced or filled products, the substances pretreated with the silanes of the invention are wetted with resins containing aliphatic unsaturated monomers, such as, for example, polyester styrene resins, and the combination is solidified by polymerization.

The boundary surface between the resin and the inorganic material is formed, on the one hand by the reaction of the unsaturated double bonds of the resin and of the silane, and secondary by the reaction of the silanol groups formed in the hydrolysis with the inorganic metal surface. The bodies thus obtained have very high strengths, the silanes of the invention being superior to the products previously known and used (methacrylic ester and vinyl silanes), as is shown by the experiments described hereinbelow.

The aliphatic unsaturated monomers which are suitable for the preparation of the above-described reinforced or filled combination materials include, for example, styrene, acrylonitrile-butadienestyrene, acrylonitrilestyrene, styrene-butadiene, isobutene, ethylene, propylene, vinyl acetate, vinyl chloride, vinylidene chloride and methyl methacrylate. The polymers produced by polymerization may be hard substances, such as polyester resins, or they may be elastomeric substances such as styrenebutadiene-rubber.

The oxidic and metallic surfaces for whose pretreatment the said silanes are used in accordance with the invention comprise both oxidic and metallic surfaces as well as those of synthetically made products. Examples of mineral products are asbestos, mica, quartz, corundum, diatomaceous earth, and oxides of iron, chromium and titanium.

Examples of synthetic products having oxidic surfaces are glass fibers, spun and woven glass, glass balls, electrical corundum, calcium carbonate, Fe$_2$O$_3$, and CrO$_2$. Examples of metals are Al, Fe, Zn, Mg, Sn and Ti and their alloys in which these metals are the principal components.

The silane solutions are used in concentrations between 0.05 and 5%, according to how great the specific surface area of the substance to be treated is. Normally, the oxidic or metal surface is pretreated with the silane in question in order to obtain a stronger bond with the polymer. It is also possible, however, to obtain the same effect by adding to the polymer small amounts, e.g., 0.1 to 5% of the weight of the polymer of the corresponding silane. The polymer can be either a thermosetting plastic or a thermoplastic.

In order to more fully illustrate the nature of the invention and the manner of practicing the same, the following examples are presented.

EXAMPLES

EXAMPLE 1

In a 2-liter three-necked flask, equipped with a reflux condenser, a dropper funnel, a stirrer and a device for cooling the flask, 196 g (1 mole) of γ-mercaptopropyl trimethoxysilane, 106 g (1.05 moles) of triethylamine, 10 g of hydroquinone and 1000 ml of xylene are placed and cooled with stirring at 0° C. Then 104 g (1 mole) of methacrylic acid chloride is added, drop by drop, through the dropping funnel over a period of 1 hour. After removal of the cooling device, stirring is continued for 1 hour and then the precipitated triethylammonium hydrochloride is removed by filtration. The filtrate is subjected to fractional distillation. At 127° C and a pressure of 2 Torr, 135 g (51%) of a colorless fluid passes over, which has the following properties:

| | |
|---|---|
| Molecular weight: Theoretical | 264 |
| Found | 268 |
| Index of refraction n$_D^{25}$: | 1.4511 |

| Density ($d_4^{25}$): | | 1.077 |
|---|---|---|
| Elemental analysis | Theoretical | Found |
| C | 45.4% | 45.2% |
| H | 7.6% | 7.7% |
| O | 24.2% | 24.0% |
| Si | 10.6% | 10.7% |
| S | 12.1% | 12.0% |

The product accordingly has the formula:

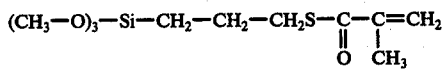

EXAMPLE 2

224 g (1 mole) of β-mercaptoethyltriethoxysilane, 106 g (1.05 moles) of triethylamine, 10 g of hydroquinone and 1000 ml of xylene are placed in the apparatus described under Example 1, and cooled to −5° C. Over a period of 1.5 hours, 104 g (1 mole) of methacrylic acid is added drop by drop. After the cooling is stopped, the mixture is stirred for another hour. The triethylammonium hydrochloride is filtered out and the filtrate is subjected to fractional distillation in vacuo.

At 104° C and at a pressure of 2 Torr, 157 g (54%) of a colorless fluid passes over, which has the following properties:

| Molecular weight: Theoretical | | 292 |
|---|---|---|
| Found | | 311 |
| Index of refraction $n_D^{25}$ | | 1.4691 |
| Density ($d_4^{25}$) | | 1.097 |
| Elemental analysis: | Theor. | Found |
| C | 49.3% | 49.0% |
| H | 8.2% | 7.9% |
| O | 21.9% | 22.3% |
| Si | 9.6% | 10.0% |
| S | 11.6% | 11.65% |

The discovered product accordingly has the formula:

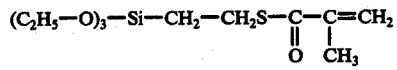

EXAMPLE 3

196 g (1 mole) of γ-mercaptopropyltrimethoxysilane, 106 g (1.05 moles) of triethylamine, 10 g of hydroquinone and 1000 ml of xylene are placed in the apparatus described in Example 1 and are cooled to −10° C. Over a period of 1.5 hours, 90 g (1 mole) of acrylic acid chloride is added, drop by drop. At +5° C, stirring is continued for 1 hour and then the triethylammonium chloride is filtered out. After the addition of 5 g of hydroquinone to the filtrate, the latter is fractionally distilled in vacuo. At 125° C and a pressure of 2 Torr, 120 g (48%) of a colorless liquid passes over, which has the following characteristics:

| Molecular weight Theor. | | 250 |
|---|---|---|
| Found | | 248 |
| Index of refraction $n_D^{25}$ | | 1.4491 |
| Density ($d_4^{25}$) | | 1.056 |
| Elemental Analysis: | Theor. | Found |
| C | 43.2% | 43.3% |
| H | 7.2% | 7.3% |
| O | 25.6% | 25.2% |
| Si | 11.2% | 10.9% |
| S | 12.8% | 12.7% |

The discovered product has the formula

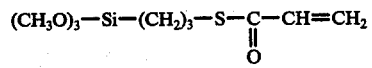

EXAMPLE 4

196 g (1 mole) of γ-mercaptopropyltrimethoxysilane, 106 g (1.05 moles) of triethylamine, 10 g of hydroquinone and 1000 ml of xylene are placed in the apparatus described in Example 1 and cooled to −10° C. Over a period of 2 hours 120 g (1.0 mole) of thiomethacrylic acid chloride is added, drop by drop, with vigorous stirring, while maintaining the reaction temperature constant. At +5° C, stirring is continued for another hour, and then the trimethylammonium chloride is separated from the filtrate. An additional 14 g of hydroquinone is added to the filtrate and the latter is fractionally distilled in vacuo. At 140° C and a pressure of 2 Torr, 59 g (21%) of a slightly yellowish liquid passes over, which has the following characteristics:

| Molecular weight Theor. | | 280 |
|---|---|---|
| Found | | 278 |
| Index of refraction $n_D^{25}$ | | 1.4702 |
| Density ($d_4^{25}$) | | 1.10 |
| Elemental analysis: | Theor. | Found |
| C | 42.8% | 42.5% |
| H | 7.1% | 7.0% |
| O | 17.1% | 16.9% |
| Si | 10.0% | 9.8% |
| S | 11.4% | 11.5% |

Structural formula:

$$(CH_3-O)_3-SI-CH_2-CH_2-CH_2-S-\underset{\underset{CH_3}{|}}{\overset{\overset{S}{\|}}{C}}-C=CH_2$$

EXAMPLE 5

In a 2-liter jacketed three-necked flask connected to a thermostat and equipped with a stirrer, a dropping funnel and a reflux condenser, 122 g (1 mole) of trimethoxysilane and 250 ml of toluene are placed. 50 mg of $H_2PtCl_6 \cdot 6 H_2O$ dissolved in 10 ml of acetone, and 10 g of hydroquinone are added.

With the temperature of the flask contents at 68° C, the addition of 149 g (1.05 moles) of allyl the thiomethacrylate is started, and ends 15 minutes later. During the addition of the allyl thiomethiocrylate the temperature is held constant at 72° C by cooling. The reaction mixture is then allowed to continue reacting for 15 minutes longer, and then is cooled to room temperature. After the addition of 15 g of hydroquinone, the mixture is fractionally distilled in vacuo in the reaction evaporator. At 123° C and a pressure of 1 Torr, 135 g (51%) of a colorless fluid passes over, whose characteristics are the same as those of the substance obtained in Example 1.

EXAMPLE 6

1%, by weight, of the silane having the formula $$H_2C=CH-COS-(CH_2)_3Si(OCH_3)_3$$

plus benzoyl peroxide are added to styrene and polymerized on a glass plate. The polymer obtained sticks substantially more strongly to the glass surface than a corresponding specimen containing no silane. This good bond is sustained even when the glass is immersed in water for 4 hours at 30° C.

EXAMPLE 7

Water-dressed glass fibers are immersed in an 0.25% ethanolic solution of γ-methacrylthiopropyltrimethoxysilane, drained, and then dried for 15 minutes in a circulating air drying oven at 130° C. Then the glass fibers thus pretreated are wetted with unsaturated polyester resin and drawn into glass tubes 4 mm thick and hardened at 100° C for 2 hours. After the finished glass fiber reinforced unsaturated polyester rods were released from the glass tubes, they were cured for 15 h at 130° C and the bending strength of the rods was determined in accordance with test standard Deutsche Industrie Norm 53,452.

Furthermore, the bending strength was determined of specimens which were immersed for 72 hours in boiling water and wiped dry. For comparison, the same tests were performed using γ-methacryloxypropyltrimethoxysilane.

| % Silane in the dressing | Bending strength of glass fiber-reinforced unsaturated polyester round rods in kp/cm² | |
|---|---|---|
| | Dry | Moist |
| 0.25% γ-methacryloxypropyltrimethoxysilane | 10800 | 7400 |
| 0.25% γ-methacrylthiopropyltrimethoxysilane | 12400 | 9200 |

EXAMPLE 8

The bending strengths of glass fiber reinforced unsaturated polyester rods made as in Example 7 with the use of 0.5% solutions of the β-methacrylthioethyltriethoxysilane, and the following values were obtained.
Dry: 11400 kp/cm²
Dry: 11400 kp/cm²
Moist: 10300 kp/cm²

EXAMPLE 9

Water-dressed glass fibers are wetted as in Example 7 with unsaturated polyester resins to which 0.5% of the β-acrylothioethyltriethoxysilane has been added, and are made into glass fiber reinforced resin rods of round cross section. The bending strength values are the same as those of Example 7.

EXAMPLE 10

One weight-percent of $$H_2C=C-C-S(CH_2)_3-Si(OCH_3)_3$$
with $CH_3$ on top carbon and $S$ double-bonded below was added to a commercial varnish based on methacrylic acid ester, and the latter was then applied to glass plates air dried for 24 hours. Then the varnish was heated at 120° C for 1 hour and the adhesion was tested by the Erichsen method of criss-cross slashing. The adhesion was very good. In contrast, the adhesion of the untreated varnish to glass plates was very poor.

Similar results were obtained with aluminum plates

What is claimed is:

1. A sulfur-containing organosilicon compound of the formula $$(RO)_{4-n}-Si\left[R'-S_x-\overset{R''}{\underset{R'''}{\overset{\|}{C}}}-C=CH_2\right]_n$$

wherein
R is a $C_{1-4}$ alkyl, cycloalkyl, $C_{2-3}$ alkoxyalkyl or phenyl radical,
R' is a branched or unbranched alkylene radical having 1 to 6 carbon atoms, phenylene or benzyl radical,
R'' is an oxygen or sulfur atom
R''' is a hydrogen atom or a methyl group,
n is 1 or 2,
x is 1 or 2
or a hydrolysis product thereof.

2. A compound according to claim 1 having the formula $$(CH_3-O)_3-Si-CH_2-CH_2-CH_2-S-\underset{\underset{O}{\|}}{C}-\underset{\underset{CH_3}{|}}{C}=CH_2$$

3. A compound according to claim 1 having the formula $$(C_2H_5-O)_3-Si-CH_2-CH_2-S-\underset{\underset{O}{\|}}{C}-\underset{\underset{CH_3}{|}}{C}=CH_2$$

4. A compound according to claim 1 having the formula $$(CH_3-O)_3-Si-(CH_2)_3-S-\underset{\underset{O}{\|}}{C}-CH=CH_2$$

5. A compound according to claim 1 having the formula $$(CH_3-O)_3-Si-CH_2-CH_2-CH_2-S-\underset{\underset{S}{\|}}{C}-\underset{\underset{CH_3}{|}}{C}=CH_2$$

6. A process for the production of a sulfur-containing organosilicon compound of the general formula $$(RO)_{4-n}-Si\left[R'-S_x-\overset{R''}{\underset{R'''}{\overset{\|}{C}}}-C=CH_2\right]_n$$

wherein R, R', R'', R''', x and n having the meanings set forth in claim 1 which comprises contacting a mercapto compound of the formula $$(RO)_3-Si-R'-SH \qquad (II)$$

in which R and R' have the previously assigned significance with a compound of the general formula $$X-\underset{R''}{\underset{\|}{C}}-\underset{R'''}{\underset{|}{C}}=CH_2 \quad (III)$$

wherein R'' and R''' have the meanings given above and X represents a group which is a halogen atom, an alkoxy group, an amido group or a hydrazide group.

7. A process according to claim 6 wherein the process is carried out in the presence of a trialkylamine.

8. A process according to claim 6 carried out in the presence of a polymerization inhibitor.

9. A process according to claim 8 wherein said polymerization inhibitor is selected from the group consisting of quinone, hydroquinone and an aminophenol.

10. A process for the preparation of a sulfur-containing organosilicon compound of the general formula $$(RO)_{4-n}-Si\left[R'-S_x-\underset{R'''}{\underset{|}{C}}-\underset{}{\underset{\|}{C}}\overset{R''}{\underset{}{}}=CH_2\right]_n$$

wherein R, R', R'', R''', x and n have the meanings given in claim 1 which comprises contacting a mercapto compound of the formula $$(RO)_3-Si-R'-SH \quad (II)$$

wherein R and R' have the meanings given above with a methacrylic acid-ester, acid halide, acrylic acid ester, acrylic acid halide, an ester or acid halide of monothiomethacrylic or monothioacrylic acid.

11. A process according to claim 10 wherein γ-mercaptopropyltrimethoxysilane is reacted with methacrylic acid chloride.

12. A process according to claim 10 wherein γ-mercaptoethyltriethoxysilane is reacted with methacrylic acid.

13. A process according to claim 10 wherein γ-mercaptopropyltrimethoxysilane is reacted with acrylic acid chloride.

14. A process according to claim 10 wherein γ-mercaptopropyltrimethoxysilane is reacted with thiomethacrylic acid chloride.

15. A process according to claim 10 wherein the compound which reacts with the mercapto compound is an acid halide.

16. A process according to claim 10 wherein the compound which reacts with the mercapto compound is an ester.

17. A process for the production of a sulfur-containing organosilicon compound of the formula $$(RO)_{4-n}-Si\left[R'-S_x-\underset{R'''}{\underset{|}{C}}-\underset{}{\underset{\|}{C}}\overset{R''}{\underset{}{}}=CH_2\right]_n$$

which comprises contacting a mercapto compound of the general formula $$H_2C=CH-(CH_2)_a-S_x-\underset{R''}{\underset{|}{C}}-\underset{R'''}{\underset{|}{C}}=CH_2 \quad (IV)$$

wherein R'' and R''' have the meanings given in claim 1, and a can have any value of 0 to 4 and x can have values of 1 and 2 with a compound of the formula $$(RO)_{4-n}-Si-H_n$$

in which R has the meanings given in claim 1 in the presence of a platinum compound whereby compounds of the general formula of claim 1 are produced.

18. A process according to claim 17 wherein said mercapto compound is an alkenylthioacrylate or alkenylthiomethacrylate compound.

* * * * *

UNITED STATES PATENT AND TRADEMARK OFFICE
CERTIFICATE OF CORRECTION

PATENT NO. : 4,060,539
DATED : November 29, 1977
INVENTOR(S) : Claus-Dietrich Seiler et al It is certified that error appears in the above-identified patent and that said Letters Patent are hereby corrected as shown below:

Title page, Abstract, 2nd line after formula — change "$C_{1-4}$" (second occurrence) to -- $C_{2-4}$ --.

Col. 1, lines 25-26 — change "C 6 to C 8" to -- $C_6$ to $C_8$ --.

Col. 2, line 13 — change "The" to -- By --.

Col. 6, line 55 — change "thiomethiocrylate" to -- thiomethacrylate --.

Col. 7, line 45 — delete "Dry: 11400 kp/cm$^2$" (second occurrence).

Col. 7, line 66 — change "plates air" to -- plates and air --.

Col. 8, line 16 — change "$C_{2-3}$" to -- $C_{2-4}$ --.

Signed and Sealed this

Twenty-eighth Day of March 1978

[SEAL]

Attest:

RUTH C. MASON
Attesting Officer

LUTRELLE F. PARKER
Acting Commissioner of Patents and Trademarks